United States Patent [19]

Palaghias

[11] Patent Number: 4,684,347
[45] Date of Patent: Aug. 4, 1987

[54] METHOD OF PREVENTING THE OCCURRENCE OF CORROSION OF AMALGAM FILLING MATERIAL FOR DENTAL PURPOSES, AND AMALGAM FILLING MATERIAL THEREFOR

[75] Inventor: Georgios Palaghias, Bromma, Sweden

[73] Assignee: Landstingens Inkopscentral, LIC ek. forening, Solna, Sweden

[21] Appl. No.: 844,446

[22] Filed: Mar. 26, 1986

[51] Int. Cl.$^4$ .......................... A61K 6/04; C22C 7/00
[52] U.S. Cl. .................................. 433/228.1; 106/35; 420/527; 433/217.1
[58] Field of Search ....................... 106/35; 433/228.1; 420/526, 527

[56] References Cited

U.S. PATENT DOCUMENTS 4,064,629 12/1977 Stoner et al. ......................... 106/35
4,528,034 9/1985 Sato et al. ........................... 420/527

*Primary Examiner*—Paul Lieberman
*Assistant Examiner*—Linda D. Skaling
*Attorney, Agent, or Firm*—Armstrong, Nikaido, Marmelstein & Kubovcik

[57] ABSTRACT

The present invention relates to a method of preventing the occurrence of corrosion of amalgam filling material for dental purposes, wherein a protective layer preventing continuous precipitation of metal from the amalgam filling and consisting of metal phosphates not easily dissolved in saliva, is caused to be formed along the exposed surfaces of the amalgam filling by initially incorporating phosphate ion donators in the amalgam filling material in the existing surroundings.

The invention also relates to a dental amalgam for preventing the occurrence of corrosion, for performing the method, wherein the dental amalgam contains phosphate ion donators in a quantity of up to 0,5% phosphor calculated on the weight of the amalgam filling material.

7 Claims, No Drawings

METHOD OF PREVENTING THE OCCURRENCE OF CORROSION OF AMALGAM FILLING MATERIAL FOR DENTAL PURPOSES, AND AMALGAM FILLING MATERIAL THEREFOR

The present invention relates to a method of preventing the occurence of corrosion of amalgam filling material for dental purposes, and to a dental amalgam suitable for this purpose.

The use of dental amalgam known hitherto entails two main problems: the risk of secondary caries and the risk of oral corrosion. It has also been observed that in certain cases corrosion of the amalgam filling actively encourages the occurence of secondary caries.

In this context, secondary caries means the independent new appearance of a carious process on a surface already attacked. Secondary caries is thus often a result of the corrosion of amalgams in the oral cavity, or can be traced back to deficient condensing techniques for dental amalgam, particularly close to the preparation surfaces.

In order to find out more about the corrosion process of conventional amalgams, these were tested in some electrolytes normally occurring in the oral cavity, such as bacteria metabolites, (e.g. acetic acid, formic acid, lactic acid, ammonia), common salt, sodium sulphide, etc. As is known, these electrolytes are factors which stimulate the corrosion process. In conventional amalgam alloys containing zinc it has been found that, being the most electro-negative element in the alloy, zinc is dissolved out of the amalgam first. If there is a sufficient concentration of phosphate ions in the saliva, these ions will, together with the precipitated zinc, form a zinc phosphate deposit on the dental amalgam. However, experience has shown that the phosphate ion content in the saliva varies considerably from patient to patient and it is therefore impossible to achieve controlled formation of such a sparingly soluble protective layer. When the zinc has been dissolved out the $gamma_2$-phase (Sn-Hg) will be attacked. The tin in the $gamma_2$-phase (Sn-Hg) then forms corrosion products which are difficult to dissolve and will be precipitated on the surface of the amalgam and the quick-silver will react with the gamma phase ($Ag_3Sn$), thus forming new $gamma_1$ (Ag-Hg) and $gamma_2$ (Sn-Hg) phases. Once the zinc has been dissolved out, the rest of the alloy will be attacked.

The sparingly soluble corrosion products from the tin will also be deposited in gaps between tooth and amalgam. A limited quantity of such corrosion products may provide an acceptable seal for such gaps but large quantities of these corrosion products will force the amalgam filling out of the cavity. The confines of the amalgam filling against the surface of the tooth are thus no longer protected by tooth substance and they are therefore unavoidably broken down. This may lead to the retention of micro-organisms and ultimately to secondary caries.

Long-term studies with non-$gamma_2$ amalgams or amalgams containing a high percentage of copper have also been performed in the above mentioned electrolytes. If such alloys contain zinc, the zinc will be dissolved out first in these amalgams also. In the next stage the copper is attacked and forms soluble corrosion products in most of the electrolytes. There is, for instance, great affinity between copper and ammonia, but also between copper and organic acids. These easily dissolved corrosion products are probably the cause of the polished surfaces exhibited by non-$gamma_2$ amalgams even after being severely attacked by corrosion.

Suprisingly it has now proved possible by means of the present invention to eliminate the above-mentioned drawbacks of conventional amalgam fillings.

According to the invention, this is achieved in the method described in the introduction, by causing a protective layer preventing continuous precipitation of metal from the amalgam filling and consisting of metal phosphates not easily dissolved in saliva, to be formed along the exposed surfaces fo the amalgam filling by initially incorporating phosphate ion donators in the amalgam filling material in the existing surroundings.

According to a preferred embodiment of the invention any defects in said protective layer—caused by wear or the like—are continuously repaired by the initial homogenous inclusion of phosphate ion donators in the amalgam filling material.

Thus, immediately a defect appears in the protective layer, the layer will be replenished by the dissolved metal immediately reacting with phosphate ions to produce metal phosphates.

According to the invention copper phosphide ($Cu_3P$), tin phosphide ($Sn_4P_3$) or zinc phosphide ($Zn_3P_2$) is suitably used as phosphate ion donator.

The additive proposed according to the invention may be supplied when the amalgam alloy is being prepared or immediately before the dental amalgam is produced.

The invention also relates to dental amalgams for performning the method according to the invention and these dental amalgams are characterised in that they contain phosphate ion donators in a quantity of up to 0, 5% phosphor calculated on the weight of the dental amalgam.

The invention can be used for all amalgam alloys known hitherto.

Although the inhibiting effect on the corrosion process of the dental amalgam achieved according to the invention has not yet been fully expounded, it is assumed that the phosphate ion donator exerts an inhibiting effect by, in contact with primarily zinc dissolved out of the amalgam, forming sparingly soluble zinc phosphates, which in turn protect the amalgam filling from further metal precipitaion. Similarly, the phosphate ion donator according to the invention forms sparingly soluble copper phosphates when in contact with copper and also sparingly soluble compounds with any oxygen which may diffuse into the amalgam filling. The remainder of the amalgam alloy is thus also protected.

The inhibiting effect established according to the invention is thus achieved by the addition of, for instance, copper, tin or zinc phosphide, resulting in the formation of complex phosphate compounds containing primarily zinc or copper which, particularly in acid solutions, form permanent phosphate films consisting of $Zn_3(PO_3)_2$ and $Cu_3(PO_4)_2$, respectively.

In the case of tin and tin alloys the inhibiting effect has been found to be achieved by a layer of phosphate on the surface consisting of tin, oxygen and phosphate atoms which are strongly bound with covalent bonds. These phosphate layers prevent the release of tin ions and are the cause of an improvement in the alloy. This improvement is expressed in a positive shift of the potential.

The invention will be described more fully in the following with reference to the examples below, without being in any way limited thereto.

EXAMPLE 1

A conventional mixture of metal powder containing

| | |
|---|---|
| 26% by weight | tin |
| 2,5% by weight | copper |
| 1,5% by weight | zinc |
| and the remainder | silver | was mixed in known manner with quick-silver to give a dental amalgam. The dental amalgam thus produced was immersed in an electrolyte consisting of a 0,5% common salt solution. The electrolyte was replaced at regular intervals and analyzed to detect the occurrence of metal precipitation. The results showed that the metals in the dental amalgam were precipitated out and it was also noted that zinc was the first metal to be precipitated.

EXAMPLE 2

According to the invention a metal powder was used containing

| | |
|---|---|
| 26% by weight | tin |
| 2,5% by weight | copper |
| 1,5% by weight | zinc |
| 0,07% by weight | copper phosphide ($Cu_3P$) |
| and the remainder | silver. |

This mixture was thus the same as that used in Example 1, with the exception of the copper phosphide additive according to the invention, which corresponded to a phosphor content of 0,005% calculated on the weight of the dental amalgam. After mixing with quick-silver, a dental amalgam was obtained with was immersed in an electrolyte consisting of a 0,5% common salt solution, in the same manner as in Example 1.

The continuous measurements taken showed that the zinc in the dental amalgam was precipitated first, but that after a short while the precipitation ceased because a deposit of zinc phosphate had been obtained on the exposed surfaces of the dental amalgam.

EXAMPLE 3

Experiments using mixtures of metal powder containing varying quantities of the copper phosphide additive proposed according to the invention, i e 0,36% by weight, 0,72% by weight and 1,44% by weight, respectively, which is equivalent to 0,025%, 0,05% and 0,1% phosphor calculated on the weight of the dental amalgam, together with

| | |
|---|---|
| 26% by weight | tin |
| 2,5% by weight | copper |
| 1,5% by weight | zinc |
| and the remainder | silver | in the same was as in Example 2, showed that the metal ceased to dissolve out of the amalgam due to the formation of a protective layer. However, this occurred within a shorter time interval with increased quantities of phosphide.

EXAMPLE 4

A dental amalgam was produced by mixing the following metal powders with quick-silver:

| | |
|---|---|
| 17% by weight | tin |
| 11,5% by weight | copper |
| 1,5% by weight | zinc |
| 0,03% by weight | zinc phosphide ($Zn_3P_2$) |
| and the remainder | silver. |

With this dental amalgam a result was obtained corresponding to that in Example 2 and with alternative phosphide concentraions of 0,15, 0,3 and 0,6% by weight, respectively, the values were in agreement with Example 3.

EXAMPLE 5

A dental amalgam was produced by mixing the following metal powders with quick-silver:

| | |
|---|---|
| 28% by weight | tin |
| 28% by weight | copper |
| 1% by weight | zinc |
| 0,06% by weight | tin phosphide ($Sn_4P_3$) |
| and the remainder | silver. |

With this dental amalgam a result was obtained corresponding to that in Example 2 and with alternative phosphide concentraions of 0,30, 0,6 and 1,2% by weight, respectively, the values were in agreement with Example 3.

It has thus been established according to the invention that even additions equivalent to 0,005% by weight phosphor calculated on the weight of the dental amalgam give the effects strived for in the invention.

Although the same effect can be ascertained using considerably larger amounts, it has been found that taking into consideration the other properties of the dental amalgam, such as the necessary plasticity, strength etc, the quantities added should preferably not exceed 0,5% by weight phosphor and should preferably be within the range 0,025–0,3% by weight.

I claim:

1. A method of preventing the occurrence of corrosion of amalgam filling material for dental purposes, wherein a protective layer preventing continuous precipitation of metal from the amalgam filling and consisting of metal phosphates not easily dissolved in saliva, is caused to be formed along the exposed surfaces of the amalgam filling by initially incorporating phosphate ion donators in the amalgam filling material in the existing surroundings.

2. A method according to claim 1, wherein, due to the initial homogenous inclusion of phosphate ion donators, said protective layer is caused to be continuously replenished in the event of it being worn away or the like.

3. A method according to claim 1, wherein the donator comprises compounds having a content of up to 0,5% phosphor calculated on the weight of the amalgam filling material.

4. A method according to claim 1, wherein the quantity of donator added is equivalent to 0,0005 to 0,30% by weight phosphor, preferably 0,025% by weight.

5. A method according to claim 1, wherein $Cu_3P$, $Sn_4P_3$ or $Zn_3P_2$ is used as donator.

6. A dental amalgam for preventing the occurrence of corrosion, wherein the dental amalgam contains phosphate ion donators in a quantity of up to 0,5% phosphor calculated on the weight of the amalgam filling material.

7. Dental amalgam according to claim 6, wherein the quantity of donator added is equivalent to 0,005% to 0,30% phosphor, preferably 0,025%.

* * * * *